(12) United States Patent
Qiu

(10) Patent No.: US 7,820,927 B2
(45) Date of Patent: Oct. 26, 2010

(54) PROTECTOR

(75) Inventor: Yanxiong Qiu, Shenzhen (CN)

(73) Assignee: MSEP Medical Science & Technology Development (ShenZhen) Co., Ltd., Shenzhen (CN)

( * ) Notice: Subject to any disclaimer, the term of this patent is extended or adjusted under 35 U.S.C. 154(b) by 719 days.

(21) Appl. No.: 11/831,253

(22) Filed: Jul. 31, 2007

(65) Prior Publication Data

US 2008/0029718 A1 Feb. 7, 2008

(30) Foreign Application Priority Data

Aug. 3, 2006 (CN) .................... 2006 2 0123406 U

(51) Int. Cl.
*H01H 3/16* (2006.01)
(52) U.S. Cl. ..................... 200/61.41; 200/600
(58) Field of Classification Search .............. 361/280, 361/281, 283.1–283.3, 278; 307/125, 116; 324/661, 677, 690; 200/600, 511, 512, 52 R, 200/61.41–61.44, 334

See application file for complete search history.

(56) References Cited

U.S. PATENT DOCUMENTS

| | | | | |
|---|---|---|---|---|
| 4,855,550 A | * | 8/1989 | Schultz, Jr. ................. | 200/600 |
| 5,440,290 A | * | 8/1995 | McCullough et al. ....... | 340/552 |
| 5,651,044 A | * | 7/1997 | Klotz et al. .................. | 378/117 |
| 6,320,282 B1 | * | 11/2001 | Caldwell ..................... | 307/125 |
| 6,376,939 B1 | * | 4/2002 | Suzuki et al. ............... | 307/326 |
| 6,922,153 B2 | * | 7/2005 | Pierga et al. ............. | 340/686.5 |
| 6,995,670 B2 | * | 2/2006 | Wadlow et al. ............. | 340/562 |
| 7,146,024 B2 | * | 12/2006 | Benkley, III ................ | 382/107 |
| 7,154,393 B2 | * | 12/2006 | Okushima et al. ........... | 340/562 |
| 7,172,340 B2 | * | 2/2007 | Oota .......................... | 378/189 |
| 7,263,168 B2 | * | 8/2007 | Singh et al. ................. | 378/117 |
| 7,440,290 B2 | * | 10/2008 | Matthews et al. ........... | 361/761 |
| 2004/0017210 A1 | * | 1/2004 | Johnson et al. ............. | 324/661 |

* cited by examiner

*Primary Examiner*—Michael A Friedhofer
(74) *Attorney, Agent, or Firm*—Global IP Services; Tianhua Gu

(57) ABSTRACT

The present invention provides a protector, especially a radiotherapeutic protector. The protector comprises a conductive baseplate with one side covered with an insulation layer and another side is mounted with a plentiful of antennae, and an electric connector is coupled on one end of the conductive baseplate. In one embodiment, the conductive baseplate is enveloped by the insulation layer, and the antennae penetrate through the insulation layer and connect to one side of the conductive baseplate. The protector of the present invention has the advantages of simplify in structure and low in price, and can effectively avoid the physical contact or collision between the radioactive source and the patient during treatment.

5 Claims, 2 Drawing Sheets

PROTECTOR

CROSS REFERENCE TO RELATED PATENT APPLICATION

This application claims the priority of the Chinese patent application No. 200620123406.X, filing date of Aug. 3, 2006.

FIELD OF THE INVENTION

The present invention relates to a protector, particularly, relates to a radiotherapeutic protector.

BACKGROUND OF THE INVENTION

For traditional radiotherapy device, usually there has a relative movement between the body of patient and the radioactive sources. For one example, in therapy, when patient lying on the operating-table, the ray source of the radiotherapy device relatively moves around with the table, then different body part of the patient be radiated; in another example, the patient lying fixedly on the operating-table, and the table makes relative movement to the ray source, then different body part of the patient be radiated also. Nevertheless, the relative movement between the ray source and the body of the patient may cause some physical contact or collision, thus harmful to the patient.

Some radiotherapy devices already have protectors, but these protectors are with complicated structure and high cost, using the devices with such protectors for treatment will heave the economic burden on the patients.

SUMMARY OF THE INVENTION

The object of the invention is to provide a protector for using in radiotherapy device to prevent the contact or touch between the radioactive source and the patient, the protector is with simple structure and low cost.

The technical solution of the present invention is, provides a protector comprising a conductive baseplate which one side of the baseplate is covered with an insulation layer and another side is mounted with a plentiful of conductive antennae, and an electric connector is coupled to the conductive baseplate.

Advantageously, the conductive baseplate is made of conductive silica gel.

Advantageously, the conductive baseplate is made of conductive rubber.

Advantageously, the conductive baseplate is made of interweaved wire net.

Advantageously, the electric connector connects with a low-voltage input signal supply.

The proctor of the present invention has the advantages of simplify in structure and low in cost, in operating, just covering the protector on the patient, with the side that has a plentiful of antennae exposes to outside, and the electric connector is linked with a low-voltage input signal supply. If the radiotherapy device touching the antennae on its movement, the protector will make out an electric signal, the signal transmitted to the radiotherapy device, then the device will cease moving, by this way, it can avoid the physical contact or collision between the radioactive source and the patient.

The protector of the present invention can be used in other fields to prevent unwanted touch between specific articles also.

DETAILED DESCRIPTION OF THE PREFERRED EMBODIMENT

Figure 1:
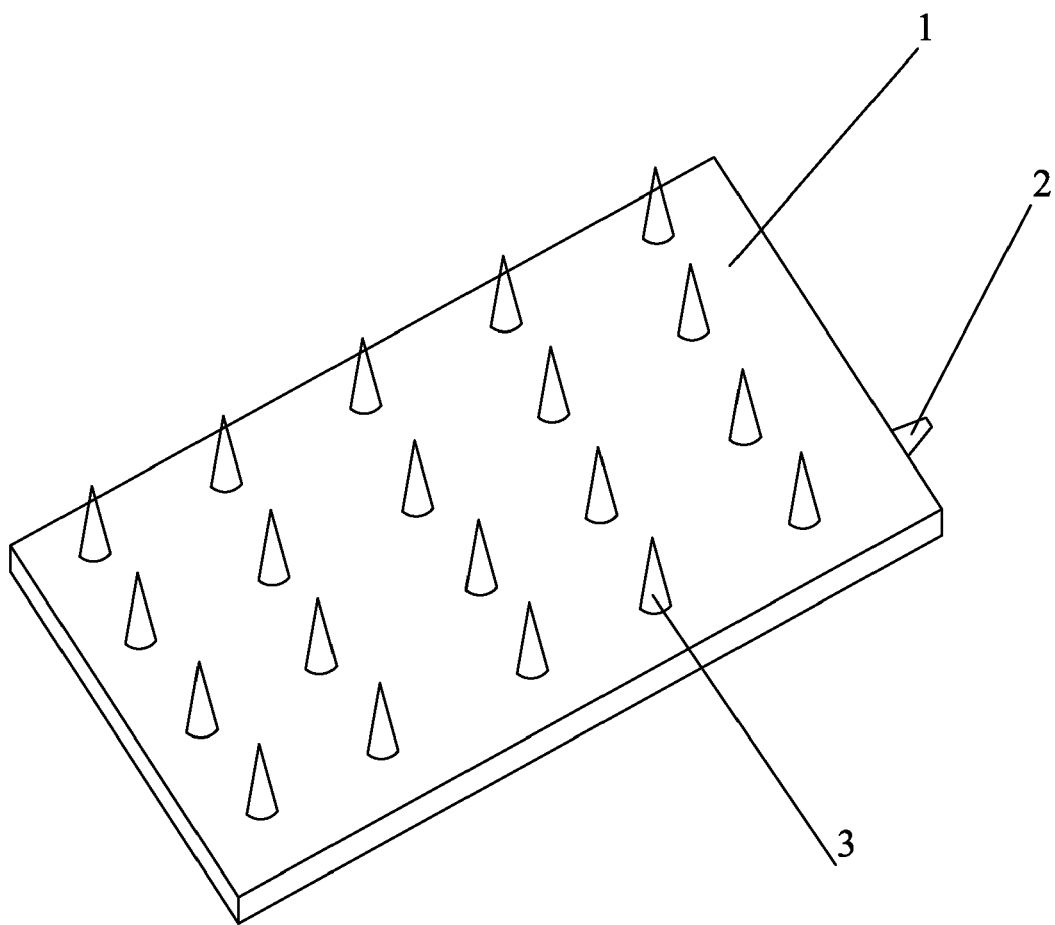
FIG. 1 is the schematic view of the protector of the present invention.
Figure 2:
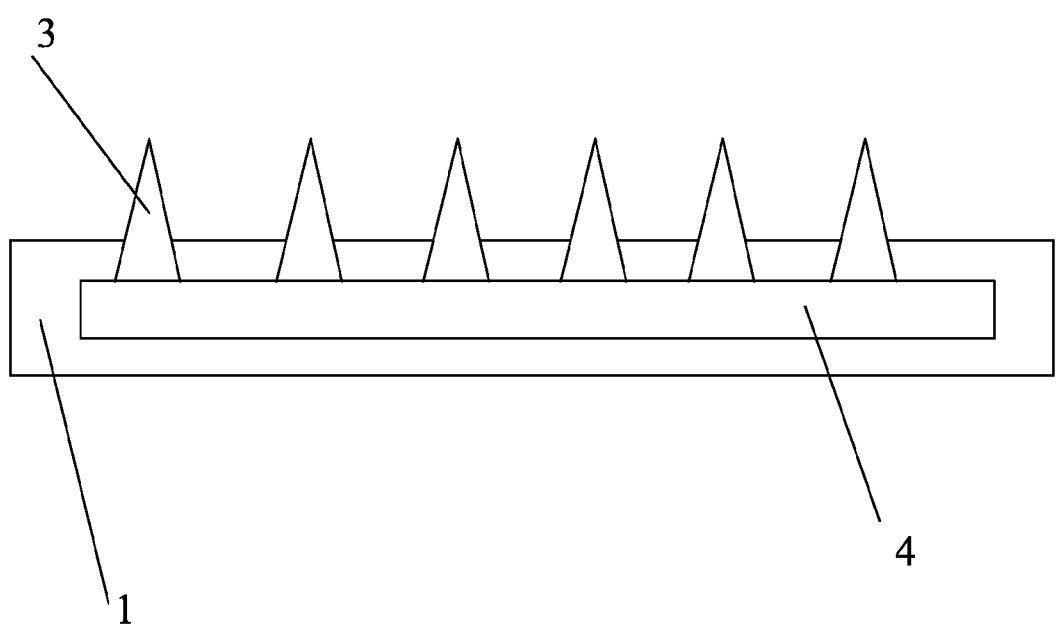
FIG. 2 is the sectional view of the protector of the present invention.

FIG. 1 is the schematic view of one embodiment of the protector in the present invention, and FIG. 2 is the corresponding sectional view. As shown in FIG. 1 and FIG. 2, the conductive baseplate 4 is enveloped by the an insulation layer 1, an electronic connector 2 that links to a low-voltage input signal supply (not show) is coupled to one side of the conductive baseplate 4. A plentiful of antennae 3 penetrate through the insulation layer 1 and be arranged on one side of the conductive baseplate 4.

In operating, covering the protector on the patient with the side that having antennae 3 exposes to outside, and the electric connector 2 is linked with a low-voltage input signal supply. If the radiotherapy touching the antennae 3 when in moving, the protector will make out an electric signal, and the radiotherapy device will cease moving once it receives such signal, thus to avoid the physical contact or collision between the radioactive source and the patient.

In one possible embodiment, the conductive baseplate 4 is made of conductive silica gel, and the insulation layer 1 is made of insulative rubber. Both of them are soft enough to cover closely on the body of the patient, which resulting in more effectively controlling the space between the radioactive source and the patients.

In another possible embodiment, the conductive baseplate 4 is made of conductive rubber, and the insulation layer 1 is made of insulative rubber.

In even another embodiment of the invention, the conductive baseplate 4 is an interweaved wire net, and the insulation layer 1 is made of insulative rubber.

In a further embodiment of the invention, the conductive baseplate 4 is made of conductive rubber with one side covered with an insulative layer and another side conductively mounted with a plentiful of antennae, and the size of the insulative layer is larger than the conductive baseplate.

In addition, the invention also can be used in other fields to prevent unwanted touch between specific articles.

Throughout the specification the aim has been to describe the preferred embodiments of the present invention without limiting the invention to any one embodiment or specific collection of features. Persons skilled in the relevant art may realize variations from the specific embodiment that will nonetheless fall within the scope of the invention.

What is claimed is:

1. A protector for preventing touch between a radioactive source and a patient comprising a conductive baseplate, one side of said conductive baseplate being covered with an insulation layer and another side being mounted with a plentiful of conductive antennae, and an electric connector being coupled on one end of the conductive baseplate, said insulation layer covering on the patient's body, said electric connector being linked with a low-voltage input signal supply, thereby, when said radioactive source touching said antennae on moving, said protector will make out an electric signal to stop said radioactive source.

2. The protector of claim 1, wherein said conductive baseplate is enveloped by said insulation layer, and said conductive antennae penetrate through said insulation layer and connect to one side of said conductive baseplate.

3. The protector of claim 2, wherein said conductive baseplate is made of conductive silica gel.

4. The protector of claim 2, wherein said conductive baseplate is made of conductive rubber.

5. The protector of claim 2, wherein said conductive baseplate is an interweaved wire net.

* * * * *